United States Patent [19]

Lindqvist et al.

[11] Patent Number: 5,262,835
[45] Date of Patent: Nov. 16, 1993

[54] METHOD AND APPARATUS FOR MAKING STEREOPHOTOGRAPHIC DOCUMENATATION AND PHOTOGRAMMETRIC MEASUREMENT OF IMPRESSIONS OR MODELS OR JAWS

[76] Inventors: Berit Lindqvist, Stugvägen 12, S-902 50 Umeå; Ulf Welander, Sofiehemsvägen 15, S-902 39, Sweden

[21] Appl. No.: 777,311
[22] PCT Filed: May 31, 1990
[86] PCT No.: PCT/SE90/00377
§ 371 Date: Jan. 30, 1992
§ 102(e) Date: Jan. 30, 1992
[87] PCT Pub. No.: WO90/14803
PCT Pub. Date: Dec. 13, 1990

[30] Foreign Application Priority Data
May 31, 1989 [SE] Sweden ............ 8901959

[51] Int. Cl.⁵ ............................. A61C 19/04
[52] U.S. Cl. ........................... 356/2; 356/243; 356/376
[58] Field of Search ............ 356/2, 376, 243; 250/558; 354/62, 112

[56] References Cited

U.S. PATENT DOCUMENTS

| | | | |
|---|---|---|---|
| 4,498,778 | 2/1985 | White | 356/243 |
| 4,837,732 | 6/1989 | Brandestini et al. | 356/376 |
| 4,858,157 | 8/1989 | Murai et al. | 356/2 |
| 4,973,114 | 11/1990 | Edwardson et al. | 356/347 |

OTHER PUBLICATIONS

Wolf, Paul R. *Elements of Photogrammetry*, McGraw Hill Book Company, New York. ©1974, p. 309.

*Primary Examiner*—Richard A. Rosenberger
*Attorney, Agent, or Firm*—Cushman, Darby & Cushman

[57] ABSTRACT

A method of making stereophotographic documentation and photogrammetric of impressions or of models of jaws, in which the impression or the model of a jaw is placed on a reference object, which in its turn is placed on a bottom plate in a photo device. The photo device includes camera mounted in a frame at a distance from the bottom plate and a light source for illuminating the impression or model on the reference object. A picture of the impression or the model of a jaw is taken by means of the camera, when the camera has position at a predetermined given reference angle distance from the vertical line. A second picture is taken of the impression or the model of a jaw after the camera has been moved to a corresponding position on the other side of the vertical line. The two pictures are placed on a tray which is intended is cooperate with a stereoscope in such a way that the two pictures can be seen three-dimensionally in the stereoscope. The pictures are brought to cooperate with a dator, which is so programmed that three-dimensional coordinates for picture points can be determined, which makes determination of desired distances and angles possible. Also relates to an apparatus which is usable for carrying out.

5 Claims, 1 Drawing Sheet

METHOD AND APPARATUS FOR MAKING STEREOPHOTOGRAPHIC DOCUMENATATION AND PHOTOGRAMMETRIC MEASUREMENT OF IMPRESSIONS OR MODELS OR JAWS

BACKGROUND OF THE INVENTION

The present invention relates to a method of making stereophotographic documentation and photogrammetric measurements of impressions or of models of jaws. The invention also relates to an apparatus useable for carrying out the method.

Within dentistry, plaster models are frequently made, which are used for visual screening and measurement of bite conditions (jaw properties), sliding callipers or the like being used for the measurement. According to current regulations, within a certain political jurisdiction about which the inventors are knowledgeable, jaw models belong to patient records and must be kept during a minimum period of three years. In most cases there is required a considerably longer storage time due to long time periods of treatment, which accordingly means that large storage spaces are needed for the plaster models during a long period of time.

Three-dimensional photographs of jaw models may to a certain extent replace plaster models. Such three-dimensional photographs may well be used for documentation, provided that measurements can be performed in these three-dimensional photographs. Thus, such photographs can be used for storage purposes instead of plaster models, which reduces the need of large storage spaces.

SUMMARY OF THE INVENTION

This invention relates to a photographic method that has been developed for documentation of jaw properties. Three-dimensional photographs are made from plaster models or impressions, the plaster models or the impressions being able to be documented in desired directions and perspectives. With the aid of computer programs desired distances and angles within the three-dimensional photographs of the jaws can be determined after measurement points have been digitized.

According to the invention, these purposes are achieved by a method of the kind mentioned by way of introduction, which in preferred practices, is characterized by the combination of the following features.

The impression or the model of a jaw is placed on a reference object which in its turn is placed on a base plate of a photographic apparatus comprising a camera mounted on a stand at a distance from the bottom plate and a light source for illuminating the article on the reference object;

One photograph of the impression or the model of a jaw is exposed with the aid of the camera when camera has taken a position at an angle distance from the vertical line, whereafter a second photograph is exposed of the impression or the model of a jaw when the camera has taken a corresponding position on the other side of the vertical line;

The two photographs are placed on a tray which is intended to cooperate with a stereoscope in such a way that the two exposed photographs may be viewed three-dimensionally in the stereoscope;

The photographs, in magnified condition, are brought to cooperate with a computer which is so programmed that three-dimensional coordinates for desired image points can be determined, which allows calculation of desired distances and angles.

BRIEF DESCRIPTION OF THE DRAWING

A preferred embodiment of an apparatus for carrying out the method is shown in the accompanying drawings, wherein.

DETAILED DESCRIPTION

Figure 1:
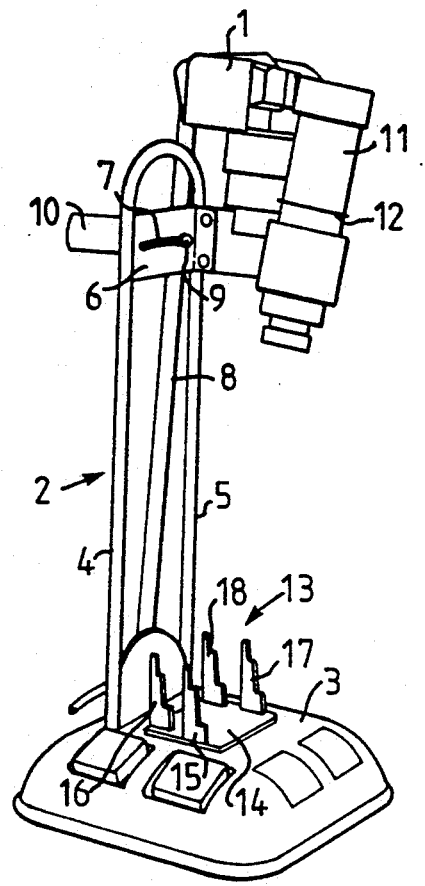
FIG. 1 shows a stereophotographic apparatus according to the invention.

In FIG. 1 there is shown stereophotografic apparatus comprising a camera arranged on a stand 2. This stand 2 comprises a base plate 3 from which two generally vertical rods 4, 5 are placed at a distance from each other and have their upper parts connected by means of a plate 6 in which there is made an arched slot 7. The lower end of a generally vertical rod 8 is pivotably arranged in the base plate 3. The camera 1 is fastened to the upper end of the rod 8 and is directed towards the central portion of the base plate. The rod 8 is intended to cooperate with the plate 6 in such a way that it can be pivoted in the vertical plane between the outer positions of the slot 7. For this purpose, there is a projection 9 arranged on the rod 8 for engagement with the slot 7.

According to this embodiment, the projection 9 comprises a screw that penetrates the rod 8 and is screwed into a handle 10 which is positioned on the other side of the rod 8. By means of the handle 10, the rod 8 can be brought along the slot 7 and be locked in a certain position. This arrangement allows the camera to be angled in relation to the base plate 3 on both sides of the vertical line so that a line drawn from the camera when the camera has taken one of its two outer positions in relation to the central portion of the base plate, forms an angle which is substantially the same as the angle which is formed when the camera has taken its other outer position on the other side of the vertical line. Due to that fact, stereo-photographs may be exposed of an object placed in the central portion of the base plate.

The photographic apparatus also comprises a projector 11, the purposes of which partly are to illuminate the object to be photographed, and partly are to be able to receive a grid indicated by the numeral 12. This grid may have a desired pattern, and its purpose is to provide land marks on the object to be photographed. The land marks facilitate the identification of the measurement points.

In FIG. 1, there is also shown a reference object 13 on which the article to be photographed is intended to be positioned. This reference object comprises a substantially planar plate 14, which is intended to be placed in the central portion of the base plate 3 in a space made for this purpose. On each side of the reference object, two stationary, narrow means located at a given distance from each other project from the plate 13. These means are indicated by the numerals 15–18 and have a step form with three levels. On each level in each means 15–18 there is made a reference point, which points accordingly will be indicated on the photographs.

Computerized measurements within the three-dimensional photographs are made possible by this arrangement with reference points. The plate 14 of the reference object 13 is preferably provided with a plus sign, i.e. two straight, perpendicular lines which are engraved on the top side of the plate 14, which is preferably made of metal. These lines have such an extension that they are seen outside the object which is intended to be photographed on the plate 14. Due to that fact, the outer portions of the lines will be indicated on the photographs.

Figure 2:
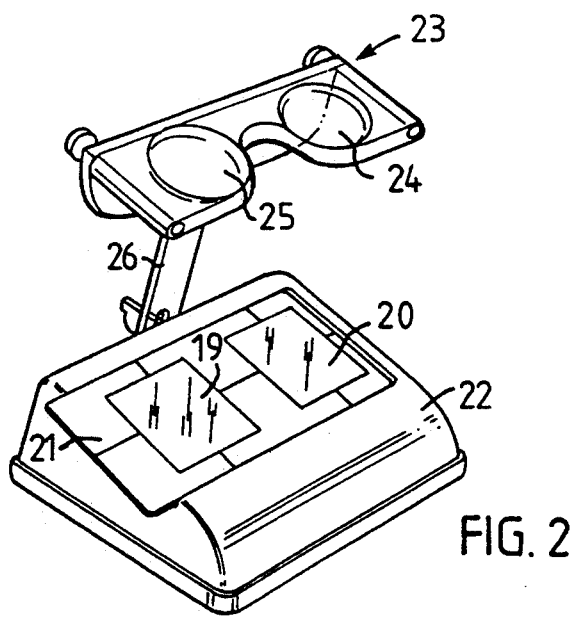
FIG. 2 shows the use of a stereoscope.

In FIG. 2, there is shown a stereoscope intended to be used when viewing two photographs 19, 20 of an object, which are exposed were taken when the rod was moved to the respective ones of its two outer positions (see FIG. 1). These two photographs are attached to a tray 21 which is intended to be placed in a space, made for this purpose and arranged in a part 22 of the stereoscope. The top side of the tray 21 is preferably provided with a straight line, which extends in the longitudinal direction of the tray, and two lines, which are substantially perpendicularly arranged in relation to the aforementioned straight line and positioned at a distance from each other so that two plus signs are formed on the top side of the tray 21. When mounting the two photographs 19, 20 on the tray 21, the photographs are arranged in that way that the perpendicular lines of the one photograph are placed on top of the one plus sign while the perpendicular lines of the second photograph are placed on top of the second plus sign. Accordingly, it is possible to orient the photographs at the mounting on the tray so that the photographs can be viewed three-dimensionally.

The stereoscope comprises a device with means 23 similar to spectacles which means is provided with two lenses 24, 25 and which is fastened to a rod 26 which in its turn is fastened to the part 22. The distance between the centres of the two photographs 19, 20 placed on the tray 20 is substantially the same as the distance between the centres of the two lenses of the stereoscope.

By viewing the two photographs in the stereoscope, a deep-viewing is possible so that a three-dimensional image of the object shown on the two photographs is received, i.e. the object is perceived in the same three-dimensional way as in reality.

Figure 3:
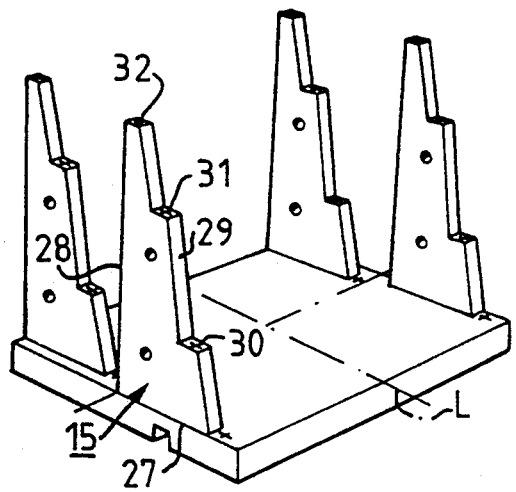
FIG. 3 shows a reference object for use in practicing the method of the invention.

In FIG. 3, the reference device is shown more closely. From this figure, it appears that each means 15-18 has a triangle-like form, with two side edges 27, 28 forming a substantially right angle to each other and with a hypotenuse 29 provided with three levels 30-32. Each pair 15, 16; 17, 18 of means has substantially the same positioning on each side of the transverse centre line L of the plate 14.

As has been mentioned previously, each level 30-32 has a reference point. Moreover, a reference point is indicated on the plate 14 in front of each means 15-18. Thus, in this case the reference object is provided with 16 reference points. By having reference points on different levels in the reference object it is possible also to make measurements in the depth direction (z-direction) by the computer. Thus, the reference object can be considered as a three-dimensional ruler.

As has been mentioned previously, a computer is intended to be utilized for measuring angles and distances. The computer programs commanding the computer reconstruct three-dimensional coordinates (x, y, z) for measurement points registered in pairs of the photographs. When the coordinates for measurement points are known, desired distances and angles may be determined. Of course, it is possible to modify the invention within the scope of the following claims. Thus, for instance, the reference object may have another form than the one shown. The essential thing is that the reference object be provided with reference points. (e.g., steps) on different levels.

If a further reference object is made that is a patrice to the above as a matrice already described reference object, the two reference objects may be put together.

If a model of the upper jaw and of the lower jaw, oriented correctly in relation to each other, are brought into the compound block of matrice and patrice and are attached to respective unit, the matrice and the patrice with models may be brought apart. The upper and the lower jaw models are then photographed separately and three-dimensional coordinates are reconstructed with available computer programs. Since the two reference objects have known, common reference points, all coordinates for the upper and lower jaw models may be brought to coincide with the coordinate system that is determined by the one or the other reference object. When this has been done, determination of distances and angles between the upper and lower jaws may be performed.

We claim:

1. A method for making stereophotographic documentation and photogrammetric measurement of articles which are impressions or models of jaws, comprising:

providing two articles which respectively are impressions or models of an upper jaw and lower jaw of a same subject;

mounting each said article in a respective reference device so that while the two reference devices have a predetermined and repeatable spatial relationship to one another, the two articles have a spatial relationship to one another which substantially corresponds to a relationship which said upper and lower jaw have to one another in said subject, each said reference device also having a like three-dimensional pattern of reference marks provided thereon;

separating said reference devices from one another while preserving spatial relations of said articles relative to respective ones of said reference devices;

taking two photographs of each said reference device-mounted article, from two respective viewpoints which are located equiangularly on opposite sides of an imaginary reference line, each at a predetermined camera-to-article distance, while projecting reference grid marks onto each said reference device-mounted article, said reference grid marks having a predetermined spatial relationship to said camera, so that each said photograph includes a picture of the respective article, and respective of said reference grid marks and said three-dimensional pattern of reference marks; and arranging said photographs in pairs, and examining said photographs using a stereoscopic viewer having a two-dimensional pattern of reference marks which correspond to a respective portion of said three-dimensional pattern of reference marks, while respective of said pairs of photographs have corresponding portions of said three-dimensional patterns of reference marks as captured therein aligned with said two-dimensional pattern of reference marks of said stereoscopic viewer, whereby distances and angles relevant to said jaws can be accurately determined from said pairs of photographs as arranged in said stereoscopic viewer.

2. Apparatus for making stereographic documentation and photogrammetric measurement of articles which are impressions or models of jaws, comprising:
a camera;
a combined camera stand and article support including a bottom plate and adjustable means for mounting the camera a given distance away from said bottom plate;
at least one reference object, said reference object being arranged to be supported at a given location on said bottom plate for supporting an article while such article is being photographed by said camera;
a light source for illuminating said article while said article is being photographed while said article is being supported on said reference object;
said adjustable means being adjustable for alternatively positioning said camera at two different positions which are respectively located equiangularly on opposite sides of an imaginary line which is perpendicular to and bisects said reference object as said given location on said bottom plate, so that said camera can be used to take two photographs of said article from respective ones of said two different positions;
said adjustable means comprising a rod pivotally mounted at one end to said bottom plate, a plate having a transversally extending slot formed therein; and a slot-following pin means mounted on said rod and received in said slot for sliding along said slot to two transversally spaced sites for defining said two different positions.

3. The apparatus of claim 2, wherein:
said pin means includes a threaded screw which projects through said slot, and a handle which threadably receives said screw and is tightenable against and loosenable from said plate having said slot, respectively for permitting and preventing pivoting of said rod relative to said bottom plate.

4. Apparatus for making stereographic documentation and photogrammetric measurement of articles which are impressions or models of jaws, comprising:
a camera;
a combined camera stand and article support including a bottom plate and adjustable means for mounting the camera a given distance away from said bottom plate;
at least one reference object, said reference object being arranged to be supported at a given location on said bottom plate for supporting an article while such article is being photographed by said camera;
a light source for illuminating said article while said article is being photographed while said article is being supported on said reference object;
said adjustable means being adjustable for alternatively positioning said camera at two different positions which are respectively located equiangularly on opposite sides of an imaginary line which is perpendicular to and bisects said reference object as said given location on said bottom plate, so that said camera can be used to take two photographs of said article from respective ones of said two different positions;
each said reference object comprising a planar plate which extends normal to said imaginary line, and four generally triangular support means, arranged with bilateral symmetry relative to said imaginary line, in a first pair having respective members located equal given distances on opposite sides of said line, and a second pair also located said equal given distances on opposite sides of said line, respective members on each side of said line being aligned in respective files; each member having three edges including a first edge disposed against said planar plate, a second edge disposed perpendicular to the respective said first edge, and a third edge arranged as a hypotenuse between distal ends of the respective said first and second edges; said third edges each being provided with a like plurality of correspondingly arranged step surfaces, in which corresponding step surfaces are disposed at uniform levels relative to said planar plate, thereby providing step surfaces at a plurality of levels.

5. The apparatus of claim 4, further including:
a second said reference object; said reference objects including cooperable with one another for providing a known, reproduceable spatial relationship of said reference objects, so that each may support in a relation corresponding to that existing in a subject, respective impressions or models of the subject's upper and lower jaws.

* * * * *